US012811012B2

(12) United States Patent
Sung et al.

(10) Patent No.: US 12,811,012 B2
(45) Date of Patent: Nov. 24, 2026

(54) BREAST CANCER RISK ASSESSMENT SYSTEM AND METHOD

(71) Applicant: SEOUL NATIONAL UNIVERSITY R&DB FOUNDATION, Seoul (KR)

(72) Inventors: Joohon Sung, Yongin-si (KR); Yu Hyun Cha, Seongnam-si (KR); Ju Young Ahn, Seoul (KR); Yeojin Jeong, Seoul (KR); Jong Won Lee, Seoul (KR)

(73) Assignee: SEOUL NATIONAL UNIVERSITY R&DB FOUNDATION, Seoul (KR)

( * ) Notice: Subject to any disclaimer, the term of this patent is extended or adjusted under 35 U.S.C. 154(b) by 271 days.

(21) Appl. No.: 18/437,377

(22) Filed: Feb. 9, 2024

(65) Prior Publication Data

US 2024/0186015 A1 Jun. 6, 2024

Related U.S. Application Data

(63) Continuation of application No. PCT/KR2021/013806, filed on Oct. 7, 2021.

(30) Foreign Application Priority Data

Aug. 12, 2021 (KR) ........................ 10-2021-0106592

(51) Int. Cl.
*G06V 10/00* (2022.01)
*G06T 7/00* (2017.01)
(Continued)

(52) U.S. Cl.
CPC ........... *G16H 50/30* (2018.01); *G06T 7/0012* (2013.01); *G06T 7/60* (2013.01); *G06V 10/70* (2022.01);
(Continued)

(58) Field of Classification Search
CPC ............ G06N 3/02; G06N 3/08; G06N 3/042; G06N 3/045; G06N 3/047; G06N 3/082;
(Continued)

(56) References Cited

U.S. PATENT DOCUMENTS 5,079,698 A * 1/1992 Grenier ................. G06T 7/0012 382/128
5,984,870 A * 11/1999 Giger .................... G06T 7/0012 600/443
(Continued)

FOREIGN PATENT DOCUMENTS

JP 2010-253245 A 11/2010
KR 10-2015-0015869 A 2/2015
(Continued)

OTHER PUBLICATIONS

Woods, "WO 03009209 A1 Computer-Aided Method and System for Detecting Spiculated Lesions in a Mammogram", date published Jan. 30, 2003.*
(Continued)

*Primary Examiner* — Amir Alavi
(74) *Attorney, Agent, or Firm* — Bridgeway IP Law Group, PLLC; Jihun Kim

(57) ABSTRACT

A breast cancer risk assessment method of a breast cancer risk assessment system using a mammography image according to an embodiment includes generating, by the breast cancer risk assessment system, assessment data including breast density information generated by measuring density of an assessment target breast from a mammography image of the assessment target breast, and breast pattern information generated by extracting a characteristic pattern of the assessment target breast from the mammography image, and calculating, by the breast cancer risk assessment system, a breast cancer occurrence risk degree of the assessment target breast by applying a preset weight to
(Continued)

each of pieces of information included in the assessment data.

15 Claims, 8 Drawing Sheets

(51) Int. Cl.
*G06T 7/60* (2017.01)
*G06V 10/70* (2022.01)
*G16H 30/20* (2018.01)
*G16H 50/30* (2018.01)

(52) U.S. Cl.
CPC .... *G16H 30/20* (2018.01); *G06T 2207/10116* (2013.01); *G06T 2207/20081* (2013.01); *G06T 2207/30068* (2013.01)

(58) Field of Classification Search
CPC ...... G06N 3/088; G06N 3/092; G06N 3/0454; G06N 3/0475; G06N 3/0464; G06N 20/00; G06N 20/10; G06N 20/20; G06T 2207/20081; G06T 2207/20084; G06T 2207/10116; G06T 2207/30068; G06T 7/507; G06T 7/0012; G06T 7/60; G16H 50/30; G16H 50/70; G16H 50/20; G16H 30/20; G16H 30/40; G16H 10/60; G06V 10/70; G06V 10/82; A61B 5/00; A61B 5/0091; A61B 5/4306; A61B 5/74
See application file for complete search history.

(56) References Cited

U.S. PATENT DOCUMENTS 6,056,690 A * 5/2000 Roberts ................. G06F 18/256
128/920
6,243,484 B1 * 6/2001 Godik .................. A61B 5/4312
382/128
7,123,762 B2 * 10/2006 Giger ..................... G06V 10/25
600/408
11,954,859 B2 * 4/2024 Glas ....................... G16H 50/70
12,367,574 B2 * 7/2025 Lotter .................... G16H 30/40
12,380,992 B2 * 8/2025 McKinney ............... G06N 3/08
12,444,048 B2 * 10/2025 Watanabe .............. G16H 50/30
12,488,899 B2 * 12/2025 Saillard .................. G16H 30/40
2011/0026791 A1 2/2011 Collins et al.
2014/0355840 A1 * 12/2014 Pearson Peyton ..... A61B 6/563
382/115
2020/0354797 A1 11/2020 Allman et al.
2024/0186015 A1 * 6/2024 Sung ...................... G16H 30/20

FOREIGN PATENT DOCUMENTS

KR 10-2208358 B1 1/2021
KR 10-2223255 B1 3/2021
KR 10-2021-0095654 A 8/2021

OTHER PUBLICATIONS

"International Search Report of PCT/KR2021/013806", May 11, 2022.
Daniel F. Schmidt et al., "Cirrus: An Automated Mammography-Based Measure of Breast Cancer Risk Based on Textural Features", JNCI Cancer Spectrum, Oct. 2018, vol. 2, No. 4, pp. 1-8.
Aimilia Gastounioti et al., "Beyond breast density: a review on the advancing role of parenchymal texture analysis in breast cancer risk assessment", Breast Cancer Research, Sep. 20, 2016, vol. 18, No. 91, pp. 1-12.
Georgia V. Ionescu et al., "Prediction of reader estimates of mammographic density using convolutional neural networks", Journal of Medical Imaging, Jan. 31, 2019, vol. 6, No. 3, pp. 031405-1-031405-15.
"Why Study Mammographic Density?", Conference Program 2020, Oct. 13, 2020.

* cited by examiner

BREAST CANCER RISK ASSESSMENT SYSTEM AND METHOD

CROSS-REFERENCE TO RELATED APPLICATION

This application is a Continuation Application of PCT/KR2021/013806, which claims priority under 35 U.S.C. § 119 to Korean Patent Application No. 10-2021-0106592, filed on Aug. 12, 2023, in the Korean Intellectual Property Office, the disclosure of which is incorporated by reference herein in its entirety.

BACKGROUND

The present disclosure relates to a breast cancer risk assessment system and method, and more specifically, to a system and method for assessing breast cancer risk by measuring breast density and extracting characteristic patterns of breast cancer development.

Breast cancer is known to be one of the most common cancers in women in Korea, along with thyroid cancer. According to data from the Central Cancer Registry Headquarters published in 2017, 19,219 cases of breast cancer occurred in 2017, which accounts for 9.0% of all cancer cases for both men and women.

Breast density, which may be measured through a mammogram to detect breast cancer, is known to be an indicator that may predict the occurrence of breast cancer. According to the results of a study conducted on Korean women, it was reported that women in the top quartile of breast density had a two to four times higher breast cancer occurrence risk degree than women in the bottom quartile. Therefore, if it is possible to implement a method for screening breast cancer high-risk groups by considering breast density during a breast cancer screening process, it will be possible to establish a customized prevention strategy for high-risk breast cancer groups and contribute to breast cancer prevention through early detection of breast cancer and improvement of voluntary environment.

Currently, the known method for most accurately assessing breast density is a semi-automated measurement method by an expert with the help of a computer program. The known method may accurately assess breast density but has a disadvantage of being labor-intensive because an expert reads the breast density with the naked eyes. Therefore, there is a need for an automatic breast density assessment method for cost-effective breast density measurement. Also, the known method has a problem of low reliability because breast density measurement values vary depending on technical conditions such as radiation dose and imaging device manufacturer.

SUMMARY

The present disclosure provides a system and method for automatically assessing breast cancer risk through breast density measurement.

Also, the present disclosure provides a system for performing a multilevel breast density assessment and pattern analysis using machine-learning-based artificial intelligence technology and assessing image-based breast cancer risk based on the multilevel breast density assessment and pattern analysis.

Also, the present disclosure provides a breast cancer risk assessment system that integrates an image-based breast cancer risk assessment result with a clinical information-based risk assessment result.

Technical objects to be achieved by the present disclosure are not limited to the technical objects described above, and other technical objects of the present disclosure may be derived from following descriptions.

According to an aspect of the present disclosure, a breast cancer risk assessment method of a breast cancer risk assessment system using a mammography image includes generating, by the breast cancer risk assessment system, assessment data including breast density information generated by measuring density of an assessment target breast from a mammography image of the assessment target breast, and breast pattern information generated by extracting a characteristic pattern of the assessment target breast from the mammography image, and calculating, by the breast cancer risk assessment system, a breast cancer occurrence risk degree of the assessment target breast by applying a preset weight to each of pieces of information included in the assessment data.

According to another aspect of the present disclosure, a breast cancer risk assessment system using a mammography image includes a communication module configured to receive the mammography image, a memory storing a breast cancer risk assessment program, and a processor configured to execute the breast cancer risk assessment program stored in the memory, wherein the processor executes the breast cancer risk assessment program to generate assessment data including breast density information generated by measuring density of an assessment target breast from a mammography image of the assessment target breast and breast pattern information generated by extracting a characteristic pattern of the assessment target breast from the mammography image and to calculate a breast cancer occurrence risk degree of the assessment target breast by applying a preset weight to each of pieces of information included in the assessment data.

BRIEF DESCRIPTION OF THE DRAWINGS

Embodiments of the inventive concept will be more clearly understood from the following detailed description taken in conjunction with the accompanying drawings in which.

DETAILED DESCRIPTION OF THE EMBODIMENTS

Figure 1:
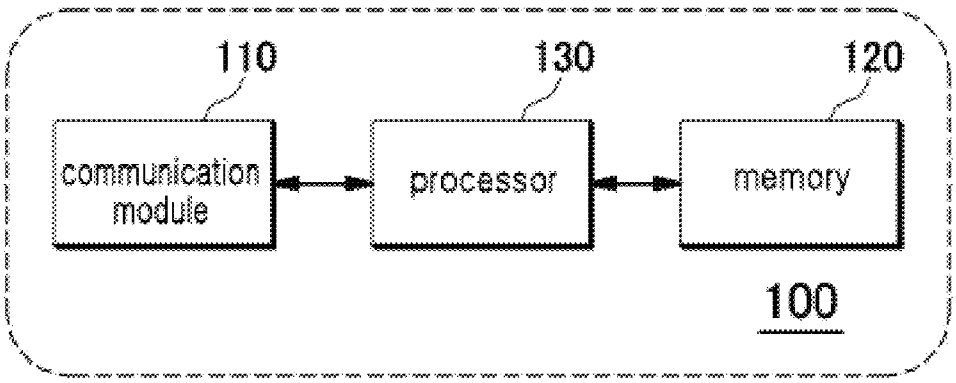
FIG. 1 is a block diagram illustrating a configuration of a breast cancer risk assessment system according to an embodiment of the present disclosure.

Hereafter, the present disclosure will be described in detail with reference to the accompanying drawings. However, the present disclosure may be implemented in many different forms and is not limited to the embodiments described herein. In addition, the accompanying drawings are only for easy understanding of the embodiments disclosed in the present specification, and the technical ideas disclosed in the present specification are not limited by the accompanying drawings. In order to clearly describe the present disclosure in the drawings, parts irrelevant to the descriptions are omitted, and a size, a shape, and a form of each component illustrated in the drawings may be variously modified. The same or similar reference numerals are assigned to the same or similar portions throughout the specification.

Suffixes "module" and "unit" for the components used in the following description are given or used interchangeably in consideration of ease of writing the specification, and do not have meanings or roles that are distinguished from each other by themselves. In addition, in describing the embodiments disclosed in the present specification, when it is determined that a detailed descriptions of related known technologies may obscure the gist of the embodiments disclosed in the present specification, the detailed descriptions are omitted.

Throughout the specification, when a portion is said to be "connected (coupled, in contact with, or combined)" with another portion, this includes not only a case where it is "directly connected (coupled, in contact with, or combined)", but also a case where there is another member therebetween. In addition, when a portion "includes (comprises or provides)" a certain component, this does not exclude other components, and means to "include (comprise or provide)" other components unless otherwise described.

Terms indicating ordinal numbers, such as first and second, used in the present specification are used only for the purpose of distinguishing one component from another component and do not limit the order or relationship of the components. For example, the first component of the present disclosure may be referred to as the second component, and similarly, the second element may also be referred to as the first component.

FIG. 1 is a block diagram illustrating a configuration of a breast cancer risk assessment system 100 according to an embodiment of the present disclosure. The breast cancer risk assessment system 100 may be implemented by a server or computing device and may operate in a cloud computing service model, such as software as a service (SaaS), platform as a service (PaaS), or infrastructure as a service (IaaS). Also, the breast cancer risk assessment system 100 may be constructed in a form, such as a private cloud system, a public cloud system, or a hybrid cloud system, but the scope of the present disclosure is not limited thereto. Although not illustrated in the drawings, the breast cancer risk assessment system 100 may transmit and receive information to and from a medical imaging device and a database storing mammography images. The breast cancer risk assessment system 100 may calculate the risk of breast cancer using mammography images-taken by a medical imaging device and a database in which the mammography images converted into big data are stored.

Referring to FIG. 1, the breast cancer risk assessment system 100 includes a communication module 110 that transmits and receives information to and from an external device and receives mammography images, a memory 120 that stores a breast cancer risk assessment program, and a processor 130 that executes a breast cancer risk assessment program stored in the memory 120. The name of the breast cancer risk assessment program is set for the sake of convenience of description, and the name itself does not limit a function of the program, and may be set as the name of one of various programs. The processor 130 may execute a program to receive a mammography image and assess and calculate breast density from the mammography image, analyze a breast pattern, set density regions based on image pixel brightness values, set clinical information based on personal information of a person having an assessment target breast, and calculate the risk of the assessment target breast based on breast density information, breast pattern information, and clinical information.

The communication module 110 described above may include a device including hardware and software required to transmit and receive signals, such as control signals or data signals, through wired or wireless connections with other network devices. The memory 120 may include a nonvolatile memory device that continuously maintains stored information even when power is not supplied and a volatile memory device that requires power to maintain the stored information. In addition, the memory 120 may perform a function of temporarily or permanently storing data and may include magnetic storage media or flash storage medium in addition to the volatile memory device that requires power to maintain the stored information, but the scope of the present disclosure is not limited thereto. The processor 130 may include various, types of devices that control and process data. Also, the processor 130 may refer to a data processing device that is built in hardware including a physically structured circuit to perform functions represented by codes or instructions included in a program. In one example, the processor 130 may include a microprocessor, a central processing unit (CPU), a processor core, a multiprocessor, an application-specific integrated circuit (ASIC), or a field programmable gate array (FPGA), or so on, but, the scope of the present disclosure is not limited thereto. A terminal may be a wireless communication device, which guarantees portability and mobility, such as a laptop computer or a desktop computer equipped with a web browser, and may include all types of a handheld-based wireless communication device, for example, a smartphones, a tablet personal computer (PC), and so on. In addition, a network may be implemented by a wired network, such as a local area network (LAN), a wide area network (WAN), or a value added network (VAN), or all types of wireless networks, such as a mobile radio communication network or a satellite communication network.

In more detail, the processor 130 may execute a breast cancer risk assessment program stored in the memory 120 to perform following functions and procedures. The processor 130 generates breast density information by measuring the density of an assessment target breast from a mammography image of the assessment target breast. The processor 130 generates assessment data including breast pattern information generated by extracting a characteristic pattern of an assessment target breast from a mammography image. The processor 130 calculates a breast cancer occurrence risk degree for an assessment target breast by applying a preset weight to each piece of information included in the assessment data. Here, the mammography image may be a digital imaging and communications in medicine (DICOM) type image. The characteristic pattern may include an abnormal breast characteristic pattern of the assessment target breast.

Also, the processor 130 executes a breast cancer risk assessment program to generate clinical information based on at least one of age information, genome information, and breast cancer family history information of a certain person corresponding to the assessment target breast. The clinical information may include physical information, female history, lifestyle habits, family history, and so on of a person having an assessment target breast. The processor 130 may perform preprocessing of adjusting a mammography image to have a preset contrast and size structure. The processor 130 may calculate a size of the assessment target breast by dividing a breast site from the pre-processed mammography image. The processor 130 may calculate breast density by using pixel density of the breast site.

Furthermore, the processor 130 may execute a breast cancer risk assessment program to divide a mammography image into a first density region, a second density region, and a third density region in descending order of brightness value according to a preset criterion of a brightness value of each pixel. In this case, the processor 130 may calculate sizes of the first to third density regions of the breast site. The size of a breast may be an area occupied by the breast in an image or an area of the breast. Also, the processor 130 may calculate breast density for each region by using the pixel density in the first to third density regions.

In one example, sizes of the breast sites of the first to third density regions may include breast size absolute values corresponding to area values of the first to third density regions of the breast site, and breast size relative values corresponding to values obtained by dividing the area values of the first to third density regions of the breast site by a total area value of the breast site.

The processor 130 may perform breast cancer risk assessment by using an artificial intelligence model using deep learning technology. In one example, the processor 130 may execute a breast cancer risk assessment program to calculate the breast density of a breast site in an image by performing a vector transformation, to which a weight is applied, based on a plurality of learning target mammography images and to generate an artificial intelligence model trained to minimize a difference between the calculated breast density and the breast density derived by an expert targeting a plurality of learning target mammography images. The processor 130 may receive a medical image of an assessment target breast by using the artificial intelligence model and measure the density of the assessment target breast. In another example, the processor 130 may execute a breast cancer risk assessment program to generate an abnormal breast pattern extraction artificial intelligence model configured to extract a characteristic pattern of an abnormal breast from the received images by performing machine learning based on mammography images of a normal person and a breast cancer patient. In this case, the processor 130 may extract an abnormal breast characteristic pattern of an assessment target breast from a mammography image by using the artificial intelligence model.

Figure 2:
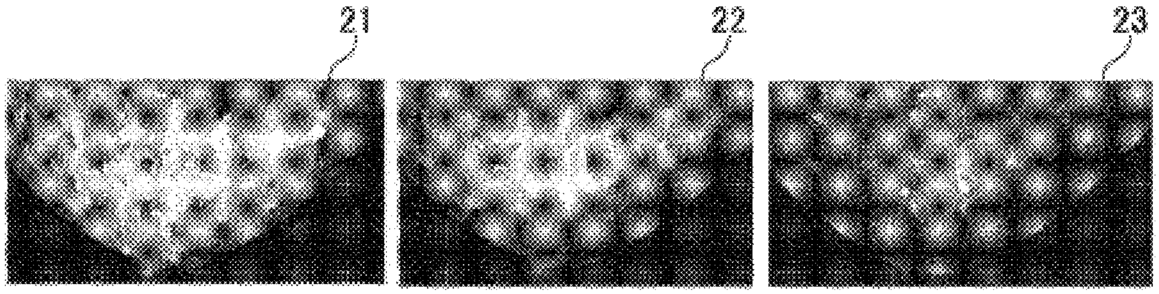
FIGS. 2 to 6 illustrate a method of analyzing mammography images, according to an embodiment of the present disclosure.
Figure 3:
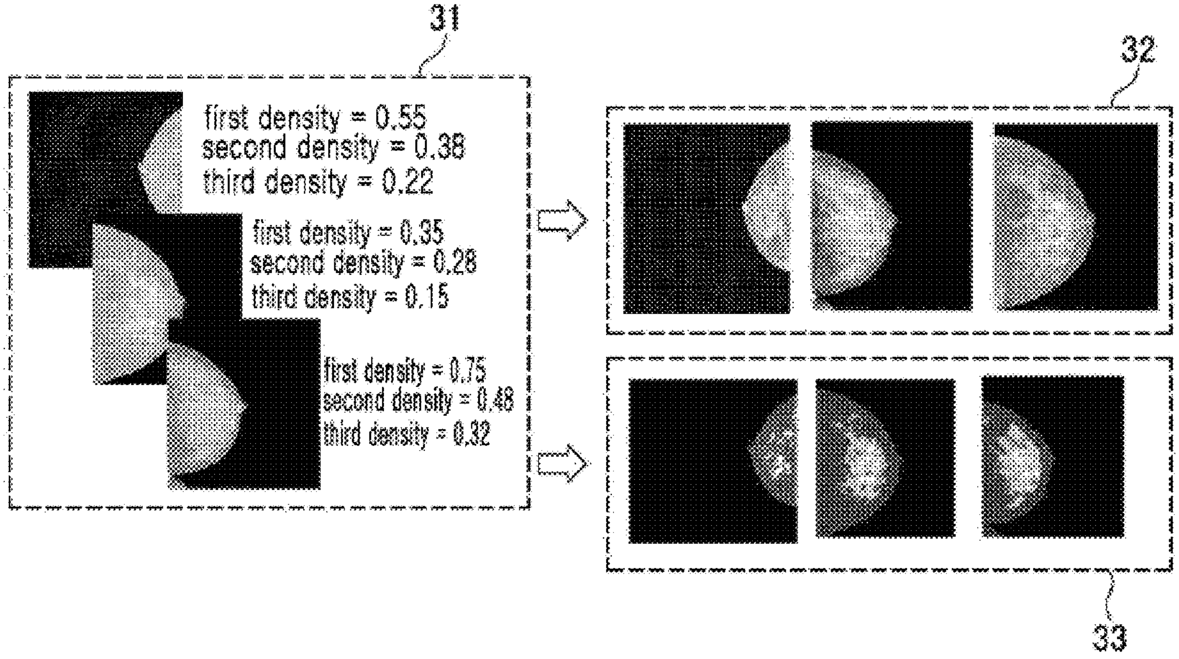

Referring to FIGS. 2 and 3 together with FIG. 1, a criterion, a basis, and a setting method for classifying the first to third density regions in a captured image of the assessment target breast are as follows. The processor 130 may assess the breast density of a target person in three stages in units of pixel. This method may be called a multilevel breast density assessment method.

For example, breast density may be classified by the processor 130 into three levels of normal density, high density and ultra-high density. The processor 130 may represent the multilevel breast density as an absolute quantity ($cm^2$) and a relative quantity (%). The absolute quantity is a value obtained by converting an absolute quantity of a breast parenchymal tissue into $cm^2$, and the relative quantity is a value obtained by dividing the absolute quantity by a total breast area and is represented as a percentage.

As illustrated in FIG. 2, the processor 130 may set the normal density as a portion 21 regarded as a parenchymal tissue in a mammography image, set the high density as a bright region 22 excluding a gray portion included in the existing normal density, and set the ultra-high density as a brightest region 23 in the image. A criterion of brightness may be set in advance. In particular, the higher the density, the higher the predictive power of breast cancer, and accordingly, the ultra-high density has a low overall ratio but reflects best the risk of breast cancer and may be used as an independent indicator due to a low correlation with the normal density. Accordingly, the processor 130 may highly assess the risk of an assessment target breast corresponding to a mammography image with many ultra-high density regions.

In FIG. 3, in a tagged image database 31 storing a mammography image, a part 21 may be set to first density, a part 22 may be set to second density, and a part 23 may be set to third density. The first to third density values may be derived by measuring density values for each density region. A pre-processing image database 32 and a segmentation image database 33 may be obtained from the tagged image database 31 respectively through a pre-processing process and an image segmentation process.

Examples of major procedures performed by the processor 130 according to the embodiment of the present disclosure described above are as follows.

The processor 130 may perform image-based risk assessment for assessing risk from a mammography image based on a machine-learning method, and clinical information-based risk assessment for assessing risk by applying a statistical method to clinical information and genomic information. The image-based risk assessment may include a breast density assessment process for automatically assessing the breast density of an input image through a weight variable, and a pattern analysis process for extracting a pattern related to breast cancer risk from the input image through a weight variable and assessing the risk therethrough.

The processor 130 may calculate an integrated breast cancer risk by combining results of image-based risk assessment and clinical information-based risk assessment. The breast density assessment process is a process of automatically assessing breast density from an input image and includes a breast segmentation process of dividing a breast site, a preprocessing process of performing size adjustment and local contrast enhancement of the input image, a dense region prediction process of predicting a dense region by performing vector transformation on the preprocessed image, and a breast density prediction process of calculating the breast density by combining results of the breast segmentation process and the dense region prediction process.

Weight variables in the breast density assessment process may be trained through a tagged image database that represents images and image analysis information. The learning process is trained by using an image preprocessed through the preprocessing process as an input image. The processor 130 separates the input image into training data and verification data, and repeats a process of adjusting a conversion weight to minimize a cost function for the training data until the cost function for the verification data is minimized, thereby adjusting the conversion weight in the dense region prediction process.

The processor 130 may output a breast density measurement value based on an output result of the breast segmentation process and a dense region prediction process during the breast density prediction process. Breast density may be calculated as breast absolute density (dense area, DA) and percent density (PD) for each density category.

The pattern analysis process performed by the processor 130 may be trained through a tagged image database that represents images and normal/patient determination information. The pattern analysis process may include a process of repeating the process of adjusting a conversion weight to minimize a cost function according to a learning process until the cost function for the verification data is minimized, like the breast density assessment process.

The image-based risk assessment process performed by the processor 130 is a process of calculating the risk by applying a conversion function for converting outputs of the breast density assessment process and the pattern analysis process into risk.

The clinical information-based risk assessment process performed by the processor 130 is a process of calculating the risk based on clinical information and genomic information of a person having a risk assessment target breast. This process includes a process in which the type of a person is divided into several phenotypes using genome/family history information and then a breast cancer occurrence risk degree according to age of each phenotype is multiplied by a relative risk estimated through clinical information.

The integrated breast cancer risk assessment process performed by the processor 130 is a process of calculating the final breast cancer risk by integrating results of the image-based risk assessment process and the clinical information-based risk assessment process. This process includes a process of calculating the risk by applying a weighted average based on the normal/patient discrimination performance of each risk assessment process for the tagged image database.

The breast density assessment process performed by the processor 130 is a method of performing more accurate prediction by directly learning image analysis information of an expert. In the related art, analysis for predicting breast density obtained by analyzing an image by an expert is performed by a statistical method, but in the present disclosure, an image segmentation database may be constructed by using an expert's breast density measurement, and a corresponding database may be trained. Therefore, because density assessment for each pixel of an image may be made, accurate and multilevel breast density assessment may be made.

In the related prior art, a method of calculating breast cancer risk by calculating predefined characteristic values from an image was mainly used. Meanwhile, in the pattern analysis process performed by the processor 130, characteristics related to breast cancer risk may be extracted through weight learning by applying a machine-learning method based on a tagged image database in this study. A pattern directly related to the occurrence of breast cancer may be extracted by the method, and accordingly, a more accurate assessment of breast cancer risk may be made. Also, according to the embodiment of the present disclosure, breast density assessment, which is visually made by a trained expert, may be automated.

Hereinafter, a specific embodiment of the breast cancer risk assessment system 100 will be described with reference to FIGS. 4 and 5 together with FIG. 1.

The breast cancer risk assessment system 100 may assess breast cancer risk through a breast density assessment process, a pattern analysis process, a standard density conversion process, an image-based risk assessment process, a clinical information-based risk assessment process, and an integrated breast cancer risk assessment process.

The breast density assessment process is a process of converting an input image into an output vector through a transformation vector, calculating the breast density (multilevel breast density) for each density category, and outputting the calculated breast density. The standard density conversion process is a process of receiving multilevel breast density, which is an output of the breast density assessment process, as an input, converting the breast density for each category into standard density obtained by standardizing age and body mass index, and outputting the converted breast density. The pattern analysis process is a process of extracting a characteristic pattern related to breast cancer risk from an input image, performing risk analysis, and outputting finally a pattern risk.

The image-based risk assessment process is a process of applying a specific coefficient to the standard density, which is an output of the standard density conversion process, and the pattern risk, which is an output of the pattern analysis process, converting the applied data into image-based risk, and outputting the converted data.

The breast density assessment process includes a breast segmentation process, a preprocessing process, a dense region prediction process, and a breast density prediction process.

In the preprocessing process, an input image may be converted into a standard image size by using bilinear interpolation, and then normalization of the image may be performed by applying contrast limited adaptive histogram equalization (CLAHE).

In this case, an image output through the preprocessing process is denoted as I(x,y). I(x,y) represents pixel intensity of an image at x, y coordinates of the image, and when the size of a standard image is w-by-h, an image may be represented by Equation 1 below.

$$0 \le (x, y) \le 1,\ x \in [1, 2, \ldots, w],\ y \in [1, 2, \ldots, h] \quad \text{Equation 1}$$

Figure 4:
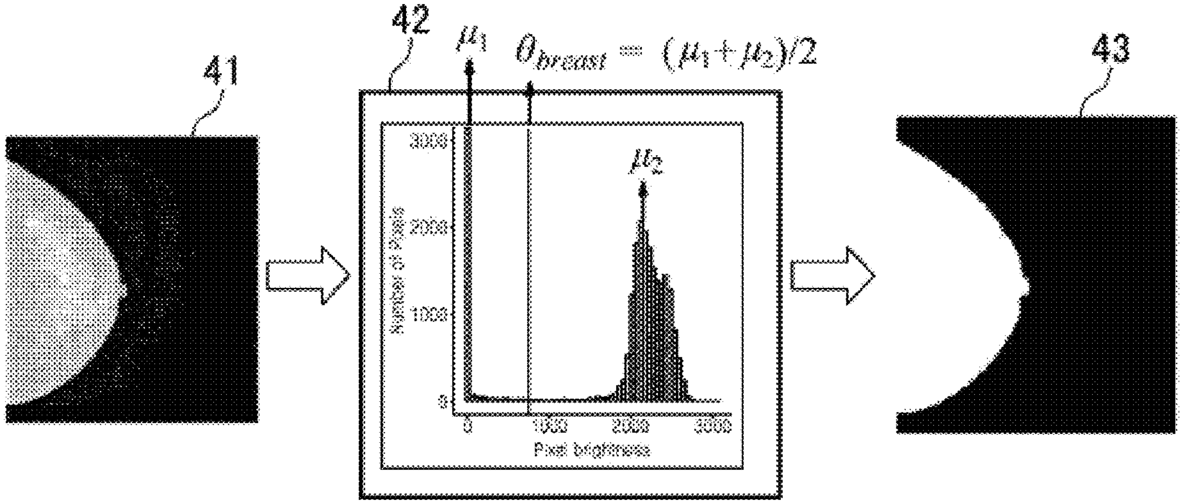
Figure 5:
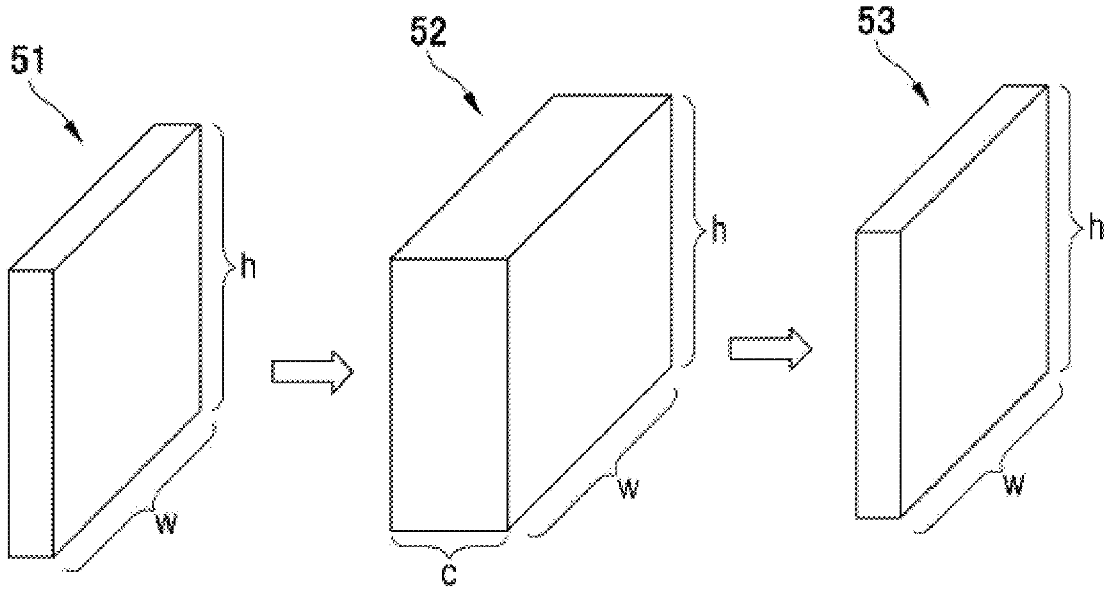

Referring to FIG. 4, in the dense region prediction process, a prediction segmentation image 43 is output by applying a conversion function 42 to an input image 41. An example of the conversion function 42 in the dense region prediction process is a linear combination of an input image and a conversion weight.

When the input image I(x,y) consists of w-by-h pixels, an input image is represented by a two-dimensional vector (having a rank w and h in each dimension) as illustrated in Equation 2. In Equation 2, xij means a (i,j)-th pixel value.

Equation 2

$$I(x, y) = (x_{11}, x_{11}, \ldots, x_{1h}, x_{21}, x_{22}, \ldots, x_{2h}, x_{w1}, x_{w2}, \ldots, x_{wh})$$

A specific example of a conversion function is a conversion function F(x,y) represented by Equation 3 below.

Equation 3

$$F(x, y) = (a_{11}, x_{11}, \ldots, a_{1h}, a_{21}, a_{22}, \ldots, a_{2h}, a_{w1}, x_{w2}, \ldots, a_{wh})$$

An output vector T(X) obtained from an input image using the conversion function F(x,y) is a w-by-h vector and has a result of element-by-element multiplication of I(x,y) and F(x,y) as elements. This may be represented by Equation 4 below.

$$T(x, y) = (x_{11} * a_{11}, x_{12} * a_{12}, \ldots, x_{wh} * a_{wh}) \quad \text{Equation 4}$$

The final output vector O(X) may be obtained by generating a total of k T(x,y) through a total of k F(x,y), concatenating the total of k T(x,y), and applying a softmax function. In this case, k is defined as the number of density categories, and an output vector O_c of category c, which is one of the k density categories, may be represented by Equation 5 below.

Equation 5

$$O_c(x, y) = \exp(T_c(x, y))/\sum_{i=U}^{k}\exp(T_i(x, y))$$

f_w may be said to be a function that is a final output vector O_c (x,y) obtained from an input image through the conversion process described above. In consideration of complexity, a convolutional operation, which is an operation used in deep-learning implementation, may be used for the conversion function f_w, and a pooling operation, a deconvolution operation, and a nonlinear function may be combined to be used.

The conversion weight F used in the dense region prediction calculation process performed by the processor 130 may be derived through a learning process as previously described with reference to FIGS. 2 and 3, and the learning process may include a process for learning a breast density assessment process based on the preprocessing image database 32 and the segmentation image database 33.

The learning process may be performed by receiving batch data generated by a batch generator. The batch generator has a function of generating batch data from the preprocessing image database and the segmentation image database and passing the batch data to the learning process to learn the breast density assessment process.

The learning process is a process of finding a conversion weight set F with the smallest cost function (loss function). This process is performed by obtaining F for minimizing the cost function for a verification set by monitoring in the process of updating W using a change in weight (W) for minimizing the cost (loss) for a training set.

The learning process adjusts a conversion weight by repeatedly performing a first process of predicting the density for each pixel by applying the current conversion weight to an input image, a second process of calculating a cost representing a difference from an expert measurement value using a cost function, and a third process of calculating a change in the conversion weight and updating the conversion weight to minimize the cost.

The learning process has a cost function, which may be represented as cost (true_label, predicted label). The cross entropy function may be used as the cost function in the learning process, but the present disclosure is not limited thereto, and the cost function may be set in various ways. In order to minimize the cost calculated by the cost function of the learning process, a change amount f_delta of the current conversion weight may be calculated and may be updated as f_new=f_old+f_delta.

In a process of minimizing the cost function for the learning data by updating the conversion weight through the learning process, the cost function for the verification data is monitored through the monitoring process. A final weight is determined by repeatedly performing the update process until a point where the cost function for the verification data is minimized.

Through the learning process and monitoring process described above, a conversion weight for best performance of the breast density assessment may be trained. Finally, a vector calculated by applying the conversion function f_w trained through the learning process to the image I(x,y) is defined as an output vector O_c (x,y), and the output vector may have a value between 0 and 1.

The output vector O_c (x,y) is a vector having, as elements, the probability that a pixel of the x,y coordinates of the input image I(x,y) belongs to each density category c, and has a range of Equation 6 below.

$$0 \le O_c(x, y) \le 1,\ x \in [1, 2, \ldots, w],\quad y \in [1, 2, \ldots, h],\ c \in [0, 1, \ldots, k] \qquad \text{Equation 6}$$

A value of c, which means a density category in the output vector O_c (x,y), is an integer between 0 and k, where 0 means a non-dense region and 1 is a density category that means density, and the larger the denser. A prediction segmentation image S_dense (x,y), which is a final output result of the dense region prediction process, is represented by Equation 7 below.

$$S_{dense}(x, y) = \arg\max_c O_c(x, y) \qquad \text{Equation 7}$$

The breast image segmentation process performed by the processor 130 is divided into a first process of converting an input image into a one-dimensional vector and a second process of segmenting the breast site in the input image by using an average of the parameter estimation values estimated by applying the Gaussian mixture model θ_breast as a threshold.

When the threshold is applied to the input image in the second process of the breast segmentation process, the input image is converted into a binary breast segmentation image output S_breast, and a breast area (BA), which is a final output of the breast segmentation process, is a value obtained by multiplying the number of total pixels of the breast area by a conversion factor K for conversion into $cm^2$.

The breast area, which is an output of a breast segmentation unit, is calculated by Equation 8 below.

$$BA(X) = k\sum_{x,y} S_{breast}(x, y) \qquad \text{Equation 8}$$

In the breast density prediction process of the breast density assessment process performed by the processor 130, a final breast density prediction result is output by combining results of a breast site and a dense region predicted from the breast segmentation process and the dense region prediction process.

A breast density output value according to the breast density prediction process is divided into absolute breast density (dense area, DA) and relative breast density (percent density, PD) for a density category.

The absolute breast density output from an input image by the breast density prediction process described above is a value obtained by multiplying the total number of pixels classified as a dense region by the conversion coefficient K for converting the unit into $cm^2$, and the absolute breast density DA_c (X) of the j-th density for the input image is obtained by Equation 9 below.

$$DA_c(X) = k\sum_{x,y} I_C(S(x, y)) \quad \text{Equation 9}$$

$$Ic(x) = \{1, x >= c \mid 0, x < c\}$$

The relative breast density (PD) output from an input image by the breast density prediction process is a value obtained by converting a ratio of an absolute breast density area (DA) to a breast area (BA) output during the breast segmentation process into percentage (%). The relative breast density PD_c (X) of the density category c for an image X is calculated by Equation 10 below.

$$PD_{(c)}(X) = \frac{DA_c(X)}{BA(X)} \times 100 \quad \text{Equation 10}$$

The standard density conversion process performed by the processor 130 is a process of converting an output of the breast density assessment process into standardized residual density. Implementation of the standard density conversion process includes a first process of performing a box-cox conversion of an output (absolute breast density and relative breast density for each density category) of the breast density assessment process, a second process of estimating the residual density by using correction variables in the results of a previous process, and a third process of calculating the standardized residual density by using μ and s, which mean respectively a sample mean and a standard deviation of the residual density obtained from expert measurement values on comparison data of the tagged image database in results of the previous process.

When one of outputs of the breast density assessment process is referred to as x, the first to third processes of the standard density conversion process may be represented by Equation 11 below.

$$x^{(\lambda)} = \frac{x^\lambda - 1}{\lambda} \quad \text{Equation 11}$$

$$R_x = x^{(\lambda)} - \left(\sum_{i=0}^{n} \alpha_i a_i\right)$$

$$(R_x)^{st} = \frac{R_x - \mu_R}{S_R}$$

$x^{(\lambda)}$ is a result of the box-cox conversion, and the conversion constant λ is estimated through maximum likelihood estimation for a normal distribution of values predicted by a correction variable while repeatedly performing conversion of expert measurement values for images of a comparison group in the tagged image database.

In Equation 11, α_i uses a coefficient estimated after fitting a linear regression model using a correction variable for the converted expert measurement value of the comparison image in the tagged image database. μ_R and S_R are values calculated from an average and a standard deviation after R_x is calculated for the comparison image.

The pattern analysis process performed by the processor 130 is a process of extracting a characteristic pattern related to breast cancer risk from an input image, performing risk analysis, and outputting finally pattern risk, and includes a preprocessing process, a pattern extraction process, and a pattern risk prediction process.

As described above, in an example of a preprocessing process, an input image may be converted into a standard image size of a width w and a height h using linear interpolation, and then contrast limited adaptive histogram equalization (CLAHE) may be applied to perform local contrast emphasis and normalization on the image.

An implementation example of the pattern extraction process performed by the processor 130 includes a convolutional neural network, and because the implementation of the convolutional neural network is a widely used technique in image processing techniques, detailed descriptions thereof are omitted, and the output may be represented as a one-dimensional vector.

The pattern risk prediction process performed by the processor 130 is a process of receiving an output of the pattern extraction process as an input and calculating breast cancer risk by using a transformation vector.

For example, a neural network model (multi-layer perceptron) may be applied to implement the pattern risk prediction process. For example, a neural network model having one hidden layer is described as an implementation example.

When an output result of the pattern extraction process is referred to as a vector X having n elements and there are an n-by-m weight vector w(1) and a vector b(1) having m elements, an output vector h of the hidden layer is represented by Equation 12 below.

$$X = (x_1, x_2, \ldots, x_n) \quad \text{Equation 12}$$

$$h = \sigma\left(w^{(1)T}x + b^{(1)}\right)$$

The pattern risk, which is the output result of the pattern extraction process, may be calculated by performing sigmoid transformation on a value obtained by applying m-by-1 weight vectors w(2) and b(2) to the hidden layer output h. An equation for calculating the final pattern risk is Equation 13 below.

$$P = \sigma\left(w^{(2)T}h + b^{(2)}\right) \quad \text{Equation 13}$$

the weights used in the pattern extraction process and the pattern risk prediction process of the pattern analysis process performed by the processor 130 may be trained through a learning process using a tagged image database. As described above, the learning process is performed by finding F that minimizes a cost function for a verification set in the process of finding a conversion weight set F having the smallest loss function value.

The image-based risk assessment process performed by the processor 130 is a process of receiving outputs of the breast density prediction process and the pattern analysis process as an input and outputting image-based risk. When outputs of the breast density prediction process are referred to as DA_i and PD_i (i=1, . . . , k) and an output of the pattern analysis process is referred to as P in a total of k density categories, an implementation example of the image-based risk assessment process may include Equation 14 below.

$$P(\text{cancer}|X) = \sigma\left(\sum_{j=0}^{k} \alpha_i DA_j + \sum_{j=0}^{k} \beta_i PD_j + \gamma P\right) \quad \text{Equation 14}$$

In Equation 14 above, α, β, and γ may be estimated from the tagged image database described above.

The clinical information-based risk assessment process performed by the processor 130 is a separate process from a process applied to mammography images, and is a process of outputting risk considering clinical information and genomic information of a target person.

There are various implementation examples of the clinical information-based risk assessment process, and in the present embodiment, a Tyrer-cuzick model, which is a model widely used in clinical practice, is used as an example. A risk calculation equation for the Tyrer-cuzick model is represented by Equation 15 below.

$$P(\text{cancer}|G) = 1 - \left(1 - \sum_{j=0}^{6} p_i F_i(t_1, t_2)\right)^{\alpha} \quad \text{Equation 15}$$

In Equation 15 above, P_i is a probability of having the i-th phenotype among six phenotypes of (absence of BRCA gene/absence of low penetrance gene), (absence of BRCA gene/presence of low penetrance gene), (presence of BRCA1 gene/absence of low penetrance gene), (presence of BRCA1 gene/presence of low penetrance gene), (presence of BRCA2 gene/absence of low penetrance gene), and (presence of BRCA2 gene/presence of low penetrance gene).

In Equation 15 above, P_i is estimated through a patient's family history of breast cancer/ovarian cancer. F_i (t_1,t_2) is a predefined value as probability that the i-th phenotype will develop breast cancer between ages t1 and t2. In Equation 15 above, a is defined as relative risk to breast cancer of a patient combining clinical information. Coefficients used in the above equations, probability of developing breast cancer at a specific age, and so on are values calculated previously based on previous research results. Because the Tyrer-cuzick model used in the clinical information-based risk assessment process is widely used to calculate breast cancer risk, detailed descriptions thereof are omitted.

The integrated breast cancer risk assessment process performed by the processor 130 is a process of calculating the breast cancer risk by combining an output of the image-based risk assessment process with an output of the clinical information-based risk assessment process. An implementation example of the integrated breast cancer risk assessment process includes a weighted average using the performance of two prediction models. The weighted average may be represented by Equation 16 below, and weights w_1 and w_2 of the integrated breast cancer assessment process may be estimated from the tagged image database described above $$P(\text{cancer}) = [w_1 * P(\text{cancer}|X) + w_2 * P(\text{cancer}|G)]/(w_1 + w_2) \quad \text{Equation 16}$$

Figure 6:
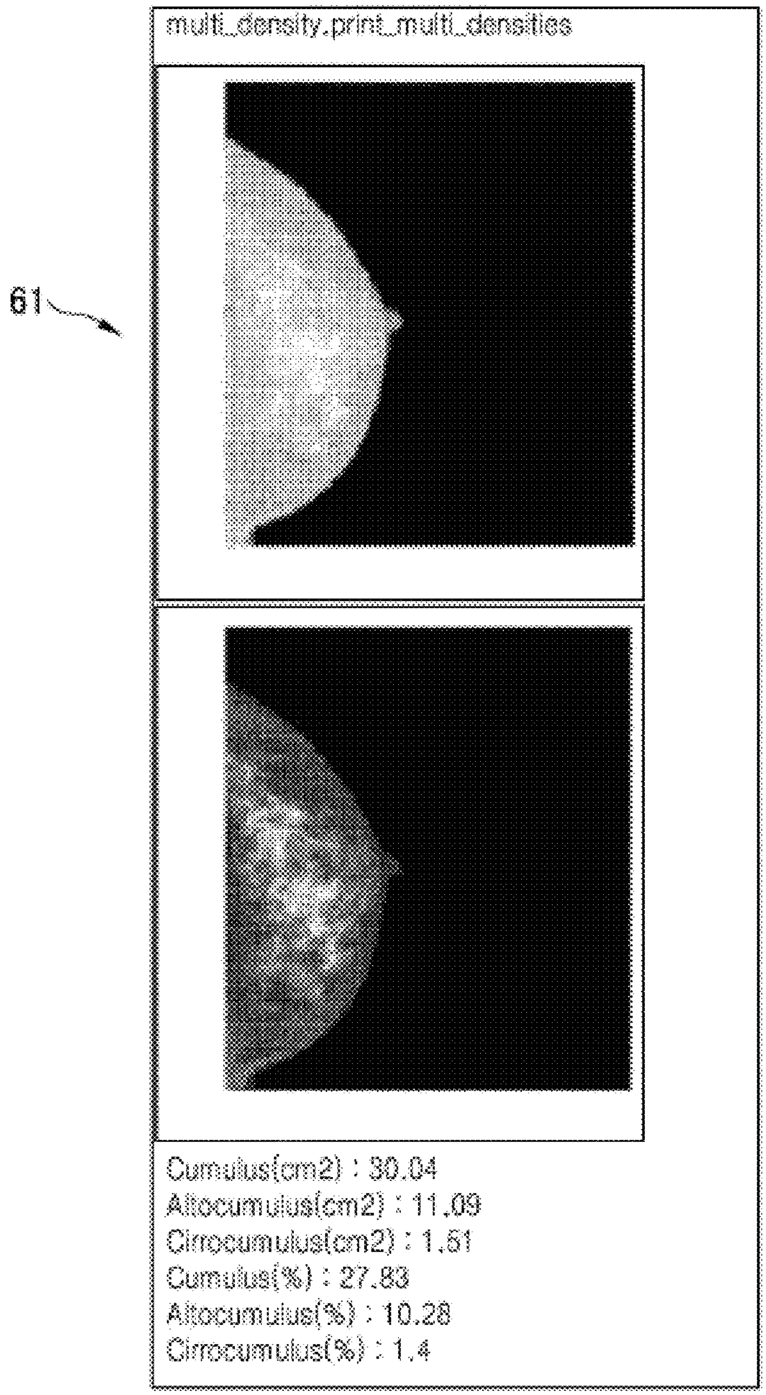

Referring to FIG. 6 in an experimental example of the present disclosure based on the above descriptions, the processor 130 may perform breast cancer risk calculation based on a mammogram-based automated risk calculation algorithm. The mammogram-based automated risk calculation algorithm includes two major categories of breast density assessment and pattern extraction, and may output mammogram-based breast cancer risk based thereon. In the corresponding experimental example, the processor 130 first performs preprocessing by using a DICOM image as an input image. Next, the processor 130 divides a breast site and calculates a total breast area of a target person. Next, the processor 130 calculates an absolute value ($cm^2$) for each multilevel breast density area and a relative value (%) compared to the total area. Next, the processor 130 may provide assessment information 61 including the final breast cancer risk based on the risk calculated through the pattern analysis process and the clinical information in addition to breast density.

Figure 7:
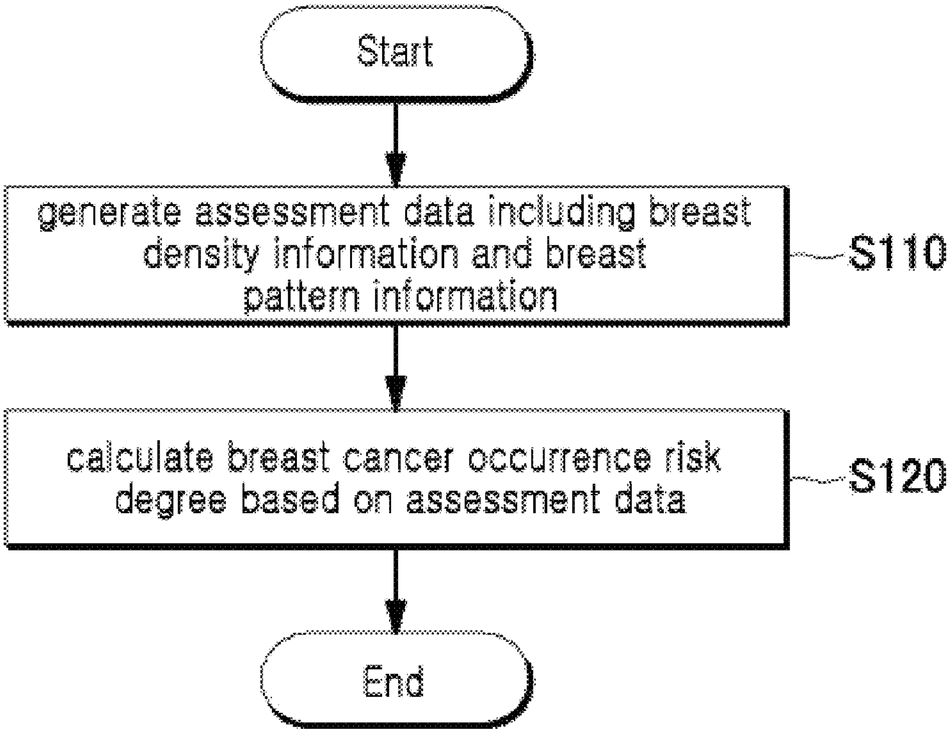
FIG. 7 is a flowchart illustrating a breast cancer risk assessment method according to an embodiment of the present disclosure.
Figure 8:
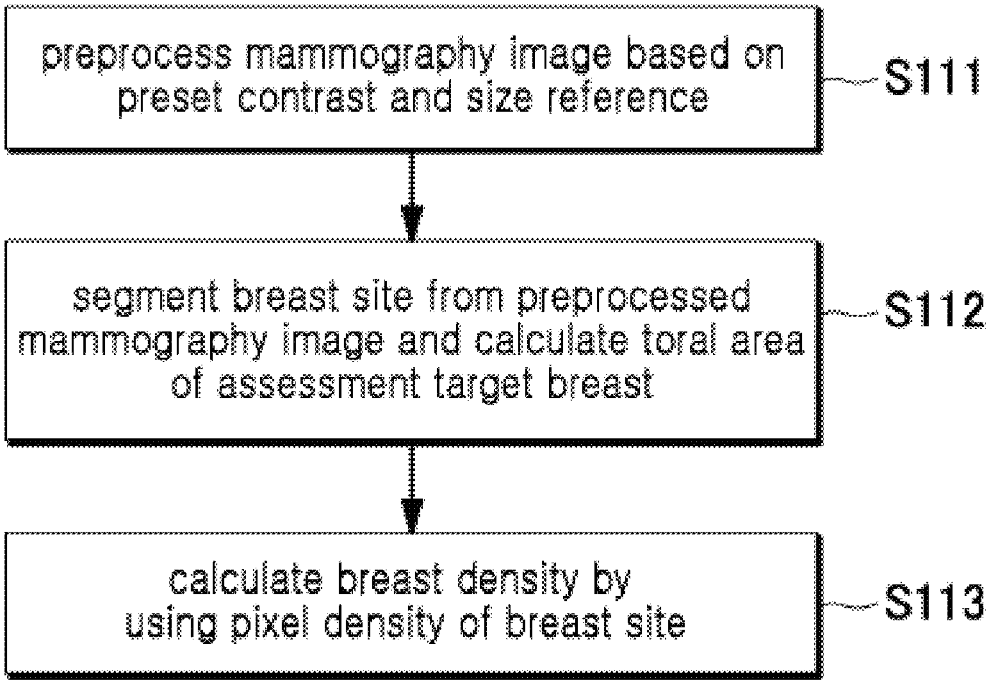
FIGS. 8 and 9 are flowcharts illustrating detailed procedures of the breast cancer risk assessment method illustrated in FIG. 7.
Figure 9:
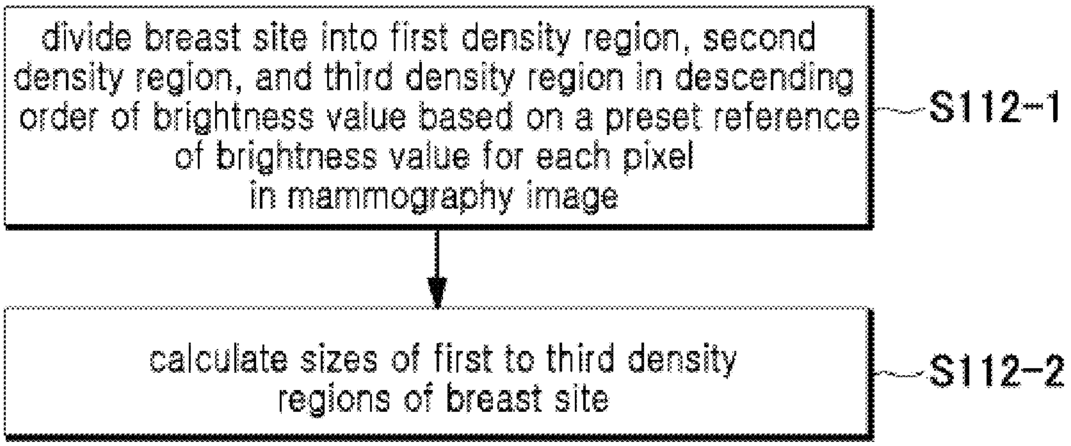

FIG. 7 is a flowchart illustrating a breast cancer risk assessment method according to an embodiment of the present disclosure, and FIGS. 8 and 9 are flowcharts illustrating detailed procedures of the breast cancer risk assessment method illustrated in FIG. 7. The breast cancer risk assessment method according to the present embodiment is a method using the breast cancer risk assessment system 100 previously described with reference to FIGS. 1 to 6. Respective steps and detailed processes of the breast cancer risk assessment method to be described below may be implemented by the breast cancer risk assessment system 100 described above and may be performed by program execution of the processor 130. Accordingly, content of the embodiment previously described with reference to FIGS. 1 to 6 may be applied equally to following embodiment, and redundant content of the above description will be omitted below.

Referring to FIG. 7 along with FIG. 1, the breast cancer risk assessment method using mammography images, according to the present embodiment, includes an assessment data generation step S110 including breast density information and breast pattern information and step S120 of calculating a breast cancer occurrence risk degree based on assessment data.

The assessment data generation step S110 is a step of generating, by the breast cancer risk assessment system 100, assessment data including the breast pattern information generated by extracting a characteristic pattern of an assessment target breast from the density information and mammography image generated by measuring density of the assessment target breast from a mammography image of the assessment target breast. Step S120 of calculating the breast cancer occurrence risk degree based on the assessment data is a step of calculating, by the breast cancer risk assessment system 100, the risk of developing breast cancer of the assessment target breast by applying a preset weight to each of the pieces of information included in the assessment data. Here, the mammography image may be a digital imaging and communications in medicine (DICOM) type image.

In one example, the assessment data generation step S110 including breast density information and breast pattern information may include a density measurement step using artificial intelligence technology. In this case, the density measurement step is a step of calculating breast density of a breast site in an image by performing weighted vector transformation based on a plurality of mammography images of a learning target, and measuring density of the assessment target breast by using an artificial intelligence model trained to minimize a difference in breast density of a breast site in an image derived by an expert from the calculated breast density and the plurality of mammography images of a learning target.

In one example, the assessment data generation step S110 including the breast density information and breast pattern information includes a pattern extraction step using artificial intelligence technology, and the characteristic pattern may include an abnormal breast characteristic pattern of the assessment target breast. In this case, the pattern extraction step may be a step of extracting the abnormal breast characteristic pattern of the assessment target breast from the plurality of mammography images by using an abnormal-breast-pattern extracting artificial intelligence model configured to extract a characteristic pattern of an abnormal breasts from an input image by performing machine learning based on a mammography image of a normal person and a breast cancer patient.

The assessment data generation step S110 may further include a step of generating, by the breast cancer risk assessment system 100, clinical information based on at least one piece of information among age information, genome information, and breast cancer family history information of a specific person corresponding to the assessment target breast. In this case, the assessment data may include clinical information.

Referring to FIG. 8, the assessment data generation step S110 including the breast density information and breast pattern information may include step S111 of performing preprocessing of a mammography image based on a preset contrast and size reference, step S112 of segmenting a breast site from the preprocessed mammography image and calculating a size of the assessment target breast, and step S113 of calculating breast density by using pixel density of the breast site. These steps may be density measurement steps. Step S113 of calculating the breast density by using the pixel density of the breast site may include a step of calculating breast density for each region by using pixel density of each of the first to third density regions.

Referring to FIG. 9, step S112 of calculating a size of an assessment target breast by segmenting a breast site from a pre-processed mammography image may include step S112-1 of dividing the breast site into a first density region, a second density region, and a third density region in descending order of brightness value based on a preset reference of the brightness value for each pixel in a mammography image, and step S112-2 of calculating sizes of the first to third density regions of the breast site. Here, a size of each of the first to third density regions of the breast site may include breast size absolute values corresponding to area values of the first to third density regions of the breast site, and breast size relative values corresponding to values obtained by dividing the area values of the first to third density regions of the breast site by a total area value of the breast site.

The breast cancer risk assessment method described above may also be implemented in the form of a recording medium including instructions that are executable by a computer, such as a program executed by a computer. Computer-readable media may be any available media that are accessible by a computer and includes both volatile and nonvolatile media and removable and non-removable media. Also, the computer-readable media may include both computer storage media and communication media. The computer storage media include both volatile and non-volatile media and removable and non-removable media implemented by any method or technology for storage of information, such as computer-readable instructions, data structures, programs, or other data.

Those skilled in the technical field to which the present disclosure pertains will be able to understand that the present disclosure may be easily modified into another specific form without changing the technical idea or essential features of the present disclosure based on the above description. Therefore, the embodiments described above should be understood in all respects as illustrative and not restrictive. The scope of the present disclosure is indicated by patent claims to be described below, and all changes or modified forms derived from the meaning and scope of the patent claims and their equivalent concepts should be construed as being included in the scope of the present disclosure.

According to the present disclosure, a highly reliable database may be constructed based on mammography image data and image analysis information (tagged image database), and breast density assessment may be automated by applying a machine-learning method to the databased data, automatic prediction of breast density may be performed by learning from a large amount of data, and a pattern that may predict occurrence of breast cancer may be extracted from the mammography image data by using patient-normal determination result information.

Also, according to the present disclosure, multilevel breast density assessment and pattern analysis may be performed by using machine-learning-based artificial intelligence technology, and the risk of breast cancer may be assessed by integrating an image-based breast cancer risk assessment result with a clinical information-based risk assessment result.

Also, according to the present disclosure, characteristics related to breast cancer risk may be extracted through weight learning by applying a machine-learning method based on a tagged image database, and thus a pattern directly related to the occurrence of breast cancer may be extracted and a more accurate assessment of breast cancer risk may be made.

Also, according to the present disclosure, breast density assessment, which was visually made by a trained expert, may be automated, and more indicators (multilevel breast density, pattern analysis, and so on) may be calculated from a breast image compared to the related art, and thus, it is possible to implement a highly efficient breast cancer risk assessment method at a relatively low cost compared to the related art.

Also, according to the present disclosure, breast cancer risk information including mammography image information may be provided to examinees in real time during the breast cancer examination process, and through the distinction between a high-risk group and a low-risk group, efficient examination resources and prevention of breast cancer may be achieved.

Effects of the present disclosure are not limited to the effects described above and include all effects understood from the above description.

BEST MODE FOR IMPLEMENTING INVENTION

The best mode for implementing the present disclosure is described above.

INDUSTRIAL APPLICABILITY

The present disclosure may be used in a medical industry related to disease diagnosis as a breast cancer diagnosis and assessment technology, thereby having industrial applicability.

What is claimed is:

1. A breast cancer risk assessment method using a mammography image performed by a processor, the breast cancer risk assessment method comprising:

generating, by a breast cancer risk assessment system, assessment data including multilevel breast density information generated by measuring multilevel density of an assessment target breast from the mammography image of the assessment target breast, and a risk pattern of breast cancer generated by extracting a characteristic pattern of the assessment target breast from the mammography image, wherein the generating the assessment data includes measuring density, wherein the measuring the density includes preprocessing the mammography image according to a preset contrast and size reference, calculating a size of the assessment target breast by dividing a breast site from the preprocessed mammography image, and calculating breast density by using pixel density of the breast site, and wherein the calculating the size of the assessment target breast comprises:

dividing the breast site into a first density region, a second density region, and a third density region in descending order of brightness according to a preset reference of a brightness value for each pixel in the mammography image; and calculating sizes of the first, second, and third density regions of the breast site.

2. The breast cancer risk assessment method of claim 1, wherein the generating the assessment data further includes generating, by the breast cancer risk assessment system, clinical information generated based on at least one of age information, genomic information, or breast cancer family history information of a certain person corresponding to the assessment target breast, and the assessment data includes the clinical information.

3. The breast cancer risk assessment method of claim 1, wherein the mammography image is a digital imaging and communications in medicine (DICOM) type image.

4. The breast cancer risk assessment method of claim 1, wherein the sizes of the first, second, and third density regions of the breast site include breast size absolute values corresponding to area values of the first, second, and third density regions of the breast site, and breast size relative values corresponding values obtained by dividing the area values of the first, second, and third density regions of the breast site by a total area value of the breast site.

5. The breast cancer risk assessment method of claim 1, wherein the calculating the breast density includes the calculating the breast density for each region by using pixel densities of the first, second, and third density regions.

6. The breast cancer risk assessment method of claim 1, wherein the generating the assessment data includes measuring the breast density by using artificial intelligence technology, and in the measuring the breast density by using the artificial intelligence technology, the density of the assessment target breast is measured by calculating a first breast density of the breast site in an image by performing weighted vector transformation based on a plurality of learning target mammography images and by using an artificial intelligence model trained to minimize a difference between the calculated breast density and a second breast density of the breast site in the image derived by an expert from the plurality of learning target mammography images.

7. The breast cancer risk assessment method of claim 1, wherein the generating the assessment data includes extracting a pattern using artificial intelligence technology, the characteristic pattern includes an abnormal breast characteristic pattern of the assessment target breast, and the extracting the pattern using the artificial intelligence technology includes extracting the abnormal breast characteristic pattern of the assessment target breast from the mammography image by using an abnormal-breast-pattern extracting artificial intelligence model configured to extract the characteristic pattern of an abnormal breast from an image input by performing machine learning based on mammography images of a normal person and a breast cancer patient.

8. A non-transitory computer-readable recording medium in which a computer program for implementing the breast cancer risk assessment method according to claim 1 is recorded.

9. A breast cancer risk assessment system using a mammography image, the breast cancer risk assessment system comprising:

a communication module configured to receive the mammography image;

a memory storing a breast cancer risk assessment program; and a processor configured to execute the breast cancer risk assessment program stored in the memory, wherein the processor executes the breast cancer risk assessment program to generate assessment data including multilevel breast density information generated by measuring multilevel density of an assessment target breast from the mammography image of the assessment target breast and a risk pattern of breast cancer generated by extracting a characteristic pattern of the assessment target breast from the mammography image, wherein the processor executes the breast cancer risk assessment program to preprocess the mammography image according to a preset contrast and size reference, calculate a size of the assessment target breast by dividing a breast site from the preprocessed mammography image, and calculate breast density by using pixel density of the breast site, and wherein the processor executes the breast cancer risk assessment program to divide the breast site into a first density region, a second density region, and a third density region in descending order of brightness according to a preset reference of a brightness value for each pixel in the mammography image, and calculate sizes of the first, second, and third density regions of the breast site.

10. The breast cancer risk assessment system of claim 9, wherein the processor executes the breast cancer risk assessment program to further perform generation of clinical information generated based on at least one of age information, genomic information, or breast cancer family history information of a certain person corresponding to the assessment target breast, and the assessment data includes the clinical information.

11. The breast cancer risk assessment system of claim 9, wherein the mammography image is a digital imaging and communications in medicine (DICOM) type image.

12. The breast cancer risk assessment system of claim 9, wherein the sizes of the first, second, and third density regions of the breast site include breast size absolute values corresponding to area values of the first, second, and third density regions of the breast site, and breast size relative values corresponding values obtained by dividing the area values of the first, second, and third density regions of the breast site by a total area value of the breast site.

13. The breast cancer risk assessment system of claim 9, wherein the processor executes the breast cancer risk assessment program to further perform calculation of the breast density for each region by using pixel densities of the first, second, and third density regions.

14. The breast cancer risk assessment system of claim 9, wherein the processor executes the breast cancer risk assessment program to further perform measurement of density of the assessment target breast by calculating a first breast density of the breast site in an image by performing weighted vector transformation based on a plurality of learning target mammography images and by using an artificial intelligence model trained to minimize a difference between the calculated breast density and a second breast density of the breast site in the image derived by an expert from the plurality of learning target mammography images.

15. The breast cancer risk assessment system of claim 9, wherein the characteristic pattern includes an abnormal breast characteristic pattern of the assessment target breast, and the processor executes the breast cancer risk assessment program to further perform extraction of the abnormal breast characteristic pattern of the assessment target breast from the mammography image by using an abnormal-breast-pattern extracting artificial intelligence model configured to extract the characteristic pattern of an abnormal breast from an image input by performing machine learning based on mammography images of a normal person and a breast cancer patient.

* * * * *